United States Patent
Dumas et al.

(10) Patent No.: US 8,168,211 B2
(45) Date of Patent: May 1, 2012

(54) USE OF A POLYPHENOL-RICH PLANT EXTRACT AS ANTIOXIDANT IN COMBINATION WITH A HYDRATING OR HUMECTANT AGENT

(75) Inventors: Marc Dumas, Saint Jean le Blanc (FR); Michèle Neveu, Orleans (FR); Béatrice Beaufrere-Seron, Olivet (FR); Jean-Hubert Cauchard, Orleans (FR); Valérie Krzych, Les Bordes (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 12/731,838

(22) Filed: Mar. 25, 2010

(65) Prior Publication Data

US 2010/0303872 A1 Dec. 2, 2010

(30) Foreign Application Priority Data

Jun. 1, 2009 (FR) ..................... 09 53608

(51) Int. Cl.
*A61K 8/00* (2006.01)
*A61K 8/97* (2006.01)
*A61K 36/738* (2006.01)

(52) U.S. Cl. ........ 424/401; 424/765; 424/774; 424/778; 424/779

(58) Field of Classification Search ......................... None
See application file for complete search history.

(56) References Cited

U.S. PATENT DOCUMENTS

| 6,093,411 | A | 7/2000 | Bissett |
| PP13,152 | P2 * | 10/2002 | Meilland |
| 2003/0170199 | A1 | 9/2003 | Leclere |
| 2006/0078568 | A1 | 4/2006 | Pauly et al. |
| 2007/0065396 | A1 | 3/2007 | Morariu |
| 2010/0209523 | A1 * | 8/2010 | Ueda ............................ 424/498 |

FOREIGN PATENT DOCUMENTS

| EP | 1243254 | | 9/2002 |
| FR | 2 768 925 | A1 | 4/1999 |
| FR | 2 918 274 | A1 | 1/2009 |
| JP | 2007-246492 | | 9/2007 |
| WO | WO 01/13879 | A1 | 3/2001 |
| WO | WO 2004/014413 | | 2/2004 |
| WO | WO 2009031694 | A1 * | 3/2009 |

OTHER PUBLICATIONS

La Giorgia (Apple icewine, last updated on Dec. 13, 2007, available at http://www.cbc.ca/news/background/food/apple-icewine.html).*
French Search Report for priority French application FR 0953608, mailed on Jan. 29, 2010.
Dumas et al., "Histological variation of Japanese skin with aging," *International Journal of Cosmetic Science* (2005) 27 (1): 47-50.
Visser et al., "Age-related change in body water and hydration in old age," *Hydration Throughout Life* (1998): 117-125.
Girard et al., "A new method for assessing, in vivo in human subjects, the basal or UV-induced peroxidation of the stratum corneum," *Skin Bioengineering Techniques and Applications in Dermatology and Cosmetology* (1998) 26: 99-107.
Dumas et al., "Hydrating skin by stimulating biosynthesis of aquaporins," *Journal of Drugs in Dermatology* (2007): s20-s24.

* cited by examiner

*Primary Examiner* — Robert A Wax
*Assistant Examiner* — Sarah Park
(74) *Attorney, Agent, or Firm* — Merchant & Gould P.C.

(57) ABSTRACT

A polyphenol-rich plant extract is used in combination with at least one hydrating or humectant agent, as cosmetic active agents in a cosmetic composition. The combination improves hydrating and antioxidant cosmetic care.

26 Claims, No Drawings

USE OF A POLYPHENOL-RICH PLANT EXTRACT AS ANTIOXIDANT IN COMBINATION WITH A HYDRATING OR HUMECTANT AGENT

This application claims the benefit of Serial No. 0953608, filed Jun. 1, 2009 in France, and which application is incorporated herein by reference. A claim of priority to all, to the extent appropriate is made.

BACKGROUND OF THE INVENTION

The present invention relates to the use of a plant extract comprising a high content of polyphenols, in particular rich in flavonoids, isoflavonoids or anthocyanins, in combination with at least one hydrating or humectant agent, as cosmetic active agent in a cosmetic composition. The invention also relates to an antiaging cosmetic composition comprising this combination of cosmetic active agents.

THE ART

Oxidative stress is a general phenomenon common to the animal and plant worlds, the consequences of which may prove to be harmful for any living creature.

Oxidative stress is a player in skin aging in man and has formed the subject of much research based on its detrimental effects at the cellular level, with the aim of preventing them or of limiting them.

Reactive oxygen species (ROSs), which are responsible for oxidative stress, are molecules formed during cellular metabolism but also after exposure to physical agents, such as UV radiation, or chemical agents, such as hydrogen peroxide.

To date, no demonstration has been set up showing that water homeostasis of the skin, that is to say the ability to maintain skin hydration at a constant level, influences aging by modulating oxidative processes at the cellular level.

It is known that disruption of water homeostasis is a very early event in skin aging. It has been shown by M. Visser and D. Gallagher in an article entitled "Age-related change in body water and hydration in old age", published in the work entitled "Hydration throughout life", M. J. Arnaud, published by John Libbey Eurotext, 1998, pages 117-125, that, generally, the body loses a large amount of water at an early stage.

It is also known that the expression of aquaporin-3 (AQP-3) in skin cells decreases with age, suggesting that the protein systems controlling the water flows are affected during aging (Dumas et al., *J. Drugs Dermatol.*, 2007, 6, 20-24, and Dumas et al., *Int. J. Cosmet. Sci.*, 2005, 27, 47-50).

SUMMARY OF THE INVENTION

The present invention is based on the hypothesis put forward by the inventors that there exists a relationship between the oxidative process, which detrimentally effects the cells of the skin and is a participant in the aging thereof, and the degree of hydration of the skin and that it would thus be possible to increase the effectiveness of antioxidants by using, as lever, the cell water and the hydrating molecules present in the skin.

Thus, by maintaining good hydration of the surface layers of the skin, epidermis and horny layer, it would be possible to substantially improve the effectiveness of endogenous antioxidant molecules or of cosmetic agents exhibiting such an antioxidant effect in order to help in reducing the oxidative processes which contribute to the aging of the skin.

The invention has thus been produced in application of these principles.

An aim of the present invention is thus to provide means for improving the effectiveness of antioxidant cosmetic agents at the skin level by combining them with cosmetic active agents capable of maintaining or reinforcing the hydration of the skin.

Another aim of the present invention is to solve the technical problem which consists in providing a combination of cosmetic active agents combining a hydration effect with a significantly increased antioxidant effect.

A further main aim of the invention is to provide a novel cosmetic composition comprising such a combination, in particular an antiaging cosmetic composition.

A further main aim of the invention is to find a solution to this technical problem in a simple and inexpensive way which can be used on an industrial and cosmetic scale.

DETAILED DESCRIPTION OF THE PREFERRED EMBODIMENTS

According to a first aspect, the present invention relates to the use of a polyphenol-rich plant extract, in combination with at least one hydrating or humectant agent, as cosmetic active agent according to the invention, in a cosmetic composition.

According to a particularly preferred implementation of the invention, the plant extract according to the invention is particularly rich in flavonoids, in isoflavonoids or in anthocyanins, which confers powerful antioxidant properties on it.

The plant material used for the preparation of the plant extract comprises one or more plant parts rich in polyphenols and in particular rich in flavonoids, in isoflavonoids or in anthocyanins.

The plant material used for the preparation of an extract according to the invention can in particular be the fruit, the flower or a part of the flower, such as the petals, or also the leaves of polyphenol-rich plants.

According to a second aspect, the present invention relates to the use of a rose extract in combination with at least one hydrating or humectant agent.

Within the meaning of the invention and in the text of the present document, the term "rose" denotes both the flower of the rose bush and, by extension, the entire plant itself and its various parts, in particular the flower and the leaves.

According to a specific alternative form, the rose extract is obtained from a rose or from a rose part naturally exhibiting a high content of anthocyanins. A preferred rose is the rose known under the Meidebenne variety name. The flower of this rose is very dark red in color. It exhibits a very high content of anthocyanins.

The Meidebenne variety is a hybrid rose variety obtained by Meilland International S.A. and protected in particular by a Community Plant Variety Right No. 7901.

In the case of the rose bush, it is the leaves and in particular the flowers which are rich in polyphenols, in particular in anthocyanins, in particular in cyanidin and pelargonidin.

The plant material for the preparation of a rose extract according to the invention is thus advantageously obtained from the whole flower, in full bloom or in bud, or a part of the flower, such as the petals, or, optionally, from the leaves.

According to a particularly preferred alternative form, the rose extract is obtained from flowers of roses of the Meidebenne variety.

The plant material can be used in the fresh state or may have been dried or dehydrated prior to the extraction stage by techniques known to a person skilled in the art.

The plant material can also be milled before the extraction stage.

The plant extract according to the invention can be prepared by various extraction processes known to a person skilled in the art and in particular those capable of extracting the polyphenols present in the plant tissues, in particular flavonoids, isoflavonoids or anthocyanins, the antioxidant properties of which are known.

According to a first alternative form, the plant extract can thus be prepared by bringing the selected plant material into contact with a polar solvent or a mixture of polar solvents.

The choice is advantageously made, as polar solvent which can be used for the extraction stage, of a solvent or a mixture of solvents chosen from water, a $C_1$-$C_4$ alcohol, for example ethanol, a $C_2$ to $C_6$ glycol preferably chosen from glycerol, butylene glycol and propylene glycol, and their mixtures.

According to a preferred implementation of the invention, use is made, for the extraction, of water, a water/glycerol mixture or a water/alcohol mixture, for example a mixture of water and of ethanol, preferably a mixture comprising more than 50% v/v of water, in particular comprising up to 90% v/v of water.

According to another alternative form of the invention, the extraction may also be carried out according to a process employing a polar solvent in the subcritical state, said solvent advantageously being water in the subcritical state.

According to yet another alternative form, the extraction can be a cryoextraction, according to a process well known to a person skilled in the art.

The extraction can also optionally comprise an additional stage consisting of a treatment of the extract targeted at partially or completely decoloring it or at purifying it, for example using a nonpolar solvent or $CO_2$ in the subcritical or supercritical state.

The extraction can be supplemented by a stage of partial or complete removal of the extraction solvents, until an aqueous concentrate devoid of significant amounts of organic solvents, or else a dry residue, is obtained.

Alternatively, the product from the extraction stage can be lyophilized or atomized in order to be provided in the form of a powder, usable in this state in a cosmetic composition or redispersed in a solvent or a mixture of solvents, in order to be used as active agent in the cosmetic compositions according to the invention.

The cosmetic composition comprises an effective amount of the abovementioned plant extract in order to obtain the desired antioxidant effect.

The tests carried out by the inventors have shown that the antioxidant properties of the plant extract according to the invention can be improved by combining it in cosmetic compositions with at least one cosmetic active agent exhibiting a hydrating or humectant effect on the skin.

The hydrating or humectant agent can be a polyol; a constituent molecule of the NMF (Naturl Moisturizing Factor) having a high affinity for water; an osmolyte; an agent which activates aquaporin biosynthesis; hyaluronic acid, in particular high molecular weight or low molecular weight hyaluronic acid, or an agent which activates the biosynthesis of hyaluronic acid, proteoglycans and CD44 hyaluronate receptors; an agent which activates the biosynthesis of lipids; an agent which activates the differentiation of keratinocytes; an agent which activates the formation of tight junctions; an agent which activates the formation of desmosomes and corneodesmosomes; an agent which activates the formation of profilaggrin and/or filaggrin and/or the natural degradation of these proteins to give NMF; or an agent which activates the formation of the horny envelope of the corneocytes.

According to an alternative embodiment, the polyol is advantageously chosen from glycerol and polyethylene glycol, alone or as mixtures.

According to another alternative embodiment, the constituent molecule of the NMF is advantageously chosen from the group consisting of constituent amino acids of filaggrin, pyrrolidonecarboxylic acid, lactate, urea, sugars, for example glucose, fructose and lactose, and trace elements, alone or as mixtures.

According to yet another alternative embodiment, the osmolyte is advantageously chosen from betaine, taurine, ornithine, lysine, inositol, trehalose, ectoine and hydroxyectoine, or extracts comprising them, or else an extract which can activate their transporters in skin cells, alone or as mixtures.

According to yet another alternative embodiment, the agent which activates aquaporin biosynthesis is advantageously chosen from those which activate aquaporin-3 (AQP-3), in particular an *Ajuga turkestanica* extract, those which activate aquaporin-9 (AQP-9), in particular a *Malva sylvestris* extract, alone or in combination with heterosides extracted from *Centella asiatica*, or those which activate another keratinocyte, melanocyte, fibroblast and adipocyte aquaporin, alone or as mixtures.

According to yet another alternative embodiment, the agent which activates the biosynthesis of hyaluronic acid and proteoglycans is advantageously D-xylose.

According to yet another alternative embodiment of the invention, the agent which activates the biosynthesis of the CD44 hyaluronate receptor is advantageously chosen from calcium salts, preferably calcium gluconate, alone or as mixtures.

According to yet another alternative embodiment, the agent which activates the biosynthesis of lipids is advantageously chosen from a *Luffa cylindrica* or sunflower seed extract or an agent which simulates the maturing and excretion of the lamellar bodies of the keratinocytes, which make it possible to improve the watertightness of the skin barrier, alone or as mixtures.

According to yet another alternative embodiment, the agent which activates the differentiation of keratinocytes is advantageously chosen from ecdysteroids, in particular β-ecdysone, or a calcium derivative, such as calcium gluconate, or pyrrolidonecarboxylic acid, or a calcium salt, alone or as mixtures.

According to yet another alternative embodiment, the agent which activates the formation of tight junctions is advantageously chosen from an *Ophiopogon japonicus* extract or a low molecular weight hyaluronic acid fraction, alone or as mixtures.

According to another alternative embodiment, the agent which activates the formation of desmosomes and corneodesmosomes is advantageously a *Lavandula stoechas* extract.

According to another alternative embodiment, the agent which activates the biosynthesis of filaggrin and profilaggrin is advantageously chosen from a *Voandzeia subterranea* extract or a *Salicornia herbacea* extract, optionally themselves advantageously combined with an agent which activates matriptase, which promotes the formation of the NMF by degradation of filaggrin, alone or as mixtures.

According to another alternative embodiment, the agent which activates the formation of the horny envelope of the corneocytes is advantageously β-ecdysone.

According to a final specific alternative embodiment, the various ways of hydrating the skin and its cells can advantageously be combined in order to maintain or reinforce the hydrating action.

According to a further aspect, the invention is also targeted at a cosmetic composition, which comprises, as cosmetic active agent according to the invention, the combination of a polyphenol-rich plant extract and of at least one hydrating or humectant agent as defined above or as resulting from the following description taken in its entirety, and is more particularly targeted at an antiaging cosmetic composition intended to alleviate or slow down signs of skin aging and in particular signs of skin aging resulting from oxidative stress and the action of ROSs.

According to one embodiment, the plant extract of this cosmetic composition is an anthocyanin-rich rose extract.

According to a specific embodiment, the concentration of plant extract of this cosmetic composition is between 0.0001% and 1% by weight of dry extract, preferably from 0.001% to 0.1% by weight of dry extract.

According to another specific embodiment, the hydrating or humectant agent of this cosmetic composition is present at a concentration of between 0.001% and 10% by weight, better still between 0.1% and 10% by weight, of the cosmetic composition.

In addition to the combination defined above, the cosmetic composition comprises at least one cosmetically acceptable excipient which can be chosen from pigments, dyes, polymers, surface-active agents, rheology agents, fragrances, electrolytes, pH adjusters, antioxidants, preservatives and their mixtures.

The cosmetic composition can be a skin care product or a make-up product and can be provided, for example, in the form of a serum, a lotion, an emulsion or also a hydrogel, in particular a mask, or can be provided in the form of a stick, for example for a lipstick, a gloss or a patch.

According to a further aspect, the invention is also targeted at a cosmetic care method, which comprises the topical application, to a concerned area of the body, of an effective amount of a cosmetic composition as defined above or in the following description, in particular for maintaining or reinforcing the state of hydration of the skin and/or for preventing or delaying the appearance of signs of aging of the skin or for slowing down the effects thereof by producing an antioxidant effect.

According to a particularly preferred alternative form of the invention, in this cosmetic care method, a cosmetic care intended to prevent or delay the appearance of signs of aging of the skin or to slow down the effects thereof, in particular intended to tone up the skin and/or to promote the softening or the resorption of the wrinkles, commonly referred to as antiaging effect, or also a care intended to protect the skin against various stresses capable of bringing about oxidation is carried out.

It is obvious to a person skilled in the art that all the embodiments or alternative embodiments of the invention in the context of the first aspect also apply to the further aspects of the invention. The alternative embodiments can be combined.

A person skilled in the art also understands that the invention thus defined makes it possible to solve the technical problem set out in the AIMS OF THE INVENTION in a satisfactory, reliable and inexpensive manner which can be used on the industrial and cosmetic scale.

Other aims, characteristics and advantages of the invention will become more clearly apparent in the light of the explanatory description which will follow, made with reference to several exemplary embodiments and tests carried out in vitro and in vivo which follow, given simply by way of illustration and which should not in any way limit the scope of the invention.

Throughout the description and in particular in the examples, the percentages are given by weight; the temperature is ambient temperature, i.e. 22° C. plus or minus 3° C.; and the pressure is atmospheric pressure, unless otherwise indicated.

EXAMPLES

Example 1 of the Invention

Cosmetic Composition According to the Invention

An oil-in-water emulsion is prepared which comprises an extract of rose flowers of the variety Meidebenne which is obtained according to a cryoextraction process. The dry extract is diluted in a water/glycerol (50/50) solution comprising 0.5% w/v of said extract.

|  | % |
| --- | --- |
| Solution of *Meidebenne* extract | 0.3 |
| Glycerol | 6.0 |
| Hydrogenated polyisobutene | 7.0 |
| Caprylic/capric triglycerides | 3.0 |
| Pentylene glycol | 3.0 |
| Glyceryl stearate | 2.5 |
| PEG-100 stearate | 2.5 |
| Beeswax | 1.5 |
| Dicaprylyl carbonate | 1.5 |
| Cetyl alcohol | 1.0 |
| Stearyl alcohol | 1.0 |
| Dimethicone | 1.0 |
| Phenoxyethanol | 0.5 |
| Xanthan gum | 0.2 |
| Acrylate/$C_{10-30}$ alkyl acrylate crosspolymer | 0.2 |
| Tetrasodium EDTA | 0.1 |
| Sodium hydroxide | <0.1 |
| Water | q.s. 100 |

The composition is prepared according to the usual methods.

The cream is used in the in vivo tests of example 2 below.

Example 2

Evaluation of the Antioxidant Properties of a Skin Care Product for Topical Application The cream prepared in example 1 (product A) is used for this in vivo study.

A cream with the same qualitative and quantitative formula, in which the glycerol of the abovementioned formula has been withdrawn and replaced by water (product B), is used as control.

The object of the study is to determine the antioxidant effects produced by each of the compositions by evaluating the reduction in reactive oxygen species (ROSs) at the surface of the skin after a topical treatment.

1—Experimental Protocol 1.1—Principle of the Measurement

Samples are withdrawn from the stratum corneum surface layers and then oxidizing species are tested using, as colored indicator, the compound DCF(H)-DA (2',7'-dichlorofluorescein diacetate), which, after deacetylation, becomes the compound DCF*, which is fluorescent in the presence of ROSs (cf., Girard et al., *Current Problems in Dermatology*, 1998, 26, pages 99-107).

The application of an antioxidant to the skin theoretically reduces the concentration of ROSs and thus reduces the fluorescence measured.

The skin is sampled using the D-Squame® standard adhesives. The D-Squame® disks are incubated in a buffer solution containing DCF* and the fluorescence is quantified by fluorimetry.

1.2—Description of the Equipment and Reagents

Device for measuring the fluorescence: Fluoroskan Ascent (Labsystems), $\lambda_{ex}$=485 nm and $\lambda_{em}$=538 nm.

96-well microplates (Labsystems: Luminostrip).

Water bath (Plexiglas, supplied by Bioblock).

D-Squame®: transparent adhesive disk with a diameter of 22 mm (Cuderm Co.) applied to the spot where the measurement is carried out at a pressure of approximately 300 gf/cm² for 10 s, using a Squameter.

Squameter (Giap): this device indicates the number of squamae sampled as a function of the factor for absorption (850 nm) of the infrared light transmitted through the D-squame® (see French patent No. FR 2 710 517 on behalf of Parfums Christian Dior).

MiniSorp plastic tubes (Polylabo).

A DCF(H)-DA solution with a concentration of $9.44 \times 10^{-4}$ M.

2.3 mg of DCF(H)-DA (Reference D-399, Molecular Probes supplied by Interchim) in 5 ml of 96° ethanol.

NaOH solution with a concentration of 0.01M (that is to say, 2 ml of an NaOH solution with a concentration of 0.5N diluted with Milli-Q water to 100 ml), pH=12 (Merck).

Phosphate buffer solution with a concentration of 66 mM, pH=7.4.

One bag of PBS (Reference P-3813, supplied by Sigma) diluted in 152 ml of Milli-Q water.

1.3—Description of the Test

—STAGE A: Deacetylation 3 ml of an NaOH solution with a concentration of 0.01M (pH=12) are added to 20 µl of the DCF(H)-DA solution described above. Reaction is allowed to take place with stirring for 100 seconds and a solution of DCF(H) (2',7'-dichlorofluorescein) is thus obtained.

STAGE B: Reaction

A D-Squame® is applied to the skin and a Squameter is used at a pressure of 300 gf/cm² for 10 s.

The D-Squame® is subsequently immersed in 1.5 ml of a phosphate buffer solution with a concentration of 66 mM (pH=7.4) in a plastic tube. A tube not comprising a D-Squame® disk is used as control.

50 µl of the DCF(H) solution prepared in stage A are added.

The tube is stirred and placed in a water bath at a temperature of 37° C. for 2 h.

250 µl of the transferred solution are placed in a well of the microplate.

The fluorescence is then read using the Fluoroskan at 37° C., $\lambda_{ex}$=485 nm and $\lambda_{em}$=538 nm.

1.4—Description of the Method

The composition is applied four times over 6 consecutive hours, i.e. once every 2 hours, to the front face of the forearms.

2 µl/cm² of the composition are applied using a fingerstall.

Three areas of skin are tested on each forearm between the elbow and the wrist.

Number of measurements repeated per area: the same solution obtained after a reaction with DCF(H) is placed in two different wells.

The stratum corneum corneocytes are collected on each forearm by stripping at t=24 h with a D-Squame® disk on each area. The analyses by fluorescence of the reactive oxygen species are carried out on the D-Squame®.

2—Statistics

The main criterion for evaluation is the measurement of the fluorescence.

A significant reduction in the fluorescence, in comparison with the untreated control, indicates a reduction in the amount of ROSs. This thus implies that the composition tested exhibits an antioxidant effect.

An analysis of variance is carried out using the ANOVA test method, the application Statgraphics Plus provided by Windows NT® being employed, with a level of significance of the test a=5%.

A statistical comparison is carried out between the fluorescence values obtained for the areas treated, on the one hand, using the composition of example 1 (product A) and, on the other hand, using the composition of example 1 without glycerol (product B).

3—Results

The results obtained are given in detail in the table of the least squares means with 95.0% confidence intervals below:

| n = 20 | Mean | Standard error | low lim | upp lim |
|---|---|---|---|---|
| Product A | 166.7 | 3.9 | 158.8 | 174.5 |
| Product B | 188.5 | 3.9 | 180.6 | 196.4 |

Statistical analysis with a 5% risk indicates a significant difference between the two means measured.

The fluorescence is on average lower for the sample treated with product A, which corresponds to the composition comprising the rose extract in combination with 6% of glycerol as humectant agent, in comparison with the composition devoid of humectant agent.

The composition combining the rose extract and the hydrating agent has a significantly greater antioxidant potential with regard to reactive oxygen species than that not comprising the combination.

This makes it possible to show that the compositions of the present invention indeed solve the technical problems posed and in particular to provide a composition exhibiting a very effective antioxidant activity.

Example 3 of Cosmetic Compositions According to the Invention

A cosmetic composition according to the invention having a hydrating or humectant and antioxidant effect, resulting in an antiaging effect, was prepared in the following way.

A lotion is prepared in the form of an aqueous solution comprising the following active principles:

The following active agents were mixed, as percentage by weight:

| | % |
|---|---|
| Solution of *Meidebenne* extract | 0.2 |
| Glycerol | 3.0 |
| *Ajuga turkestanica* extract | 0.02 |
| *Malva sylvestris* extract | 0.2 |
| *Centella asiatica* heterosides | 0.02 |
| Betaine | 1.0 |
| Glycerol | 3.0 |
| High and low molecular weight hyaluronic acids | 0.05 |
| Excipients | q.s. 100 |

The lotion is applied daily to the face.

Furthermore, a cream for the eyes is prepared in the form of an oil-in-water emulsion comprising the following active principles:

The following cosmetic active agents were mixed, as percentage by weight:

| | % |
|---|---|
| Solution of *Meidebenne* extract | 1.0 |
| *Ajuga turkestanica* extract | 0.1 |
| *Malva sylvestris* extract | 0.5 |
| *Centella asiatica* heterosides | 0.1 |
| Betaine | 1.0 |
| Glycerol | 5.0 |
| High and low molecular weight hyaluronic acids | <0.001 |
| Excipients and water | q.s. 100 |

These active ingredients are mixed in conventional fashion to produce the cosmetic composition, in this instance in the form of an oil-in-water emulsion.

Daily application of this cosmetic composition around the eyes and more particularly to the areas which may exhibit wrinkles or fine lines, for example crow's feet in the corner of the eyes, results in a significant improvement in the quality of the skin by alleviating the harmful effects of the oxidation of the skin.

The invention claimed is:

1. A cosmetic composition comprising (a) a Meidebenne rose extract containing anthocyanins and (b) at least one hydrating or humectant agent comprising glycerol.

2. The cosmetic composition of claim 1, wherein the concentration of rose extract is between 0.0001% and 1% by weight of dry extract.

3. The cosmetic composition of claim 1, wherein the concentration of rose extract is ranging between 0.001% and 0.1% by weight of dry extract.

4. The cosmetic composition of claim 1, wherein the total amount of hydrating or humectant agent is present at a concentration of between 0.001% and 10% by weight of the cosmetic composition.

5. The cosmetic composition of claim 1, wherein the total amount of hydrating or humectant agent is present at a concentration ranging between 0.01% and 10% by weight of the cosmetic composition.

6. The cosmetic composition of claim 1, wherein said at least one cosmetically acceptable excipient is selected from a pigment, a dye, a polymer, a surface-active agent, a rheology agent, a fragrance, an electrolyte, a pH adjuster, an antioxidant, a preservative; and any mixture thereof.

7. The cosmetic composition of claim 1, which is selected from a skin care product and a make-up product, provided in the form selected from a serum, a lotion, an emulsion, an hydrogel, a mask, a stick, a lipstick, a gloss and a patch.

8. The composition of claim 1, wherein said rose extract further comprises flavonoids, isoflavonoids, and mixtures thereof.

9. The composition of claim 1, wherein said rose extract is obtained from a plant part selected from whole flowers, in full bloom or in bud, from the petals, and from the leaves.

10. The composition of claim 1, wherein said extract is prepared by bringing the selected plant material into contact with a polar solvent or a mixture of polar solvents.

11. The composition of claim 10, wherein said polar solvent is selected from water, a C1-C4 alcohol, a C2 to C6 glycol, and mixtures thereof.

12. The composition of claim 10, wherein said polar solvent is selected from glycerol, butylene glycol, propylene glycol, and mixtures thereof.

13. The composition of claim 1, wherein the rose extract is obtained by cryoextraction.

14. A method of cosmetic care comprising applying, on at least one body zone in need thereof, a cosmetically effective amount of a cosmetic composition comprising (a) a Meidebenne rose extract containing anthocyanins and (b) at least one hydrating or humectant agent comprising glycerol.

15. The method of claim 14, wherein the concentration of rose extract is between 0.0001% and 1% by weight of dry extract.

16. The method of claim 14, wherein the concentration of rose extract is between 0.001% and 0.1% by weight of dry extract.

17. The method of claim 14, wherein the total amount of hydrating or humectant agent is present at a concentration of between 0.001% and 10% by weight of the cosmetic composition.

18. The method of claim 14, wherein the total amount of hydrating or humectant agent is present at a concentration ranging between 0.01% and 10% by weight of the cosmetic composition.

19. The method of claim 14, wherein said at least one cosmetically acceptable excipient is selected from a pigment, a dye, a polymer, a surface-active agent, a rheology agent, a fragrance, an electrolyte, a pH adjuster, an antioxidant, a preservative; and any mixture thereof.

20. The method of claim 14, which is selected from a skin care product and a make-up product, provided in the form selected from a serum, a lotion, an emulsion, an hydrogel, a mask, a stick, a lipstick, a gloss and a patch.

21. The method of claim 14, wherein said rose extract further comprises flavonoids, isoflavonoids, and mixtures thereof.

22. The method of claim 14, wherein said rose extract is obtained from a plant part selected from whole flowers, in full bloom or in bud, from the petals, and from the leaves.

23. The method of claim 14, wherein said extract is prepared by bringing the selected plant material into contact with a polar solvent or a mixture of polar solvents.

24. The method of claim 23, wherein said polar solvent is selected from water, a C1-C4 alcohol, a C2 to C6 glycol, and mixtures thereof.

25. The method of claim 23, wherein said polar solvent is selected from glycerol, butylene glycol, propylene glycol, and mixtures thereof.

26. The method of claim 14, wherein the rose extract is obtained by cryoextraction.

* * * * *